US009702954B2

(12) United States Patent
Ouyang et al.

(10) Patent No.: US 9,702,954 B2
(45) Date of Patent: Jul. 11, 2017

(54) PSEUDO-CONTINUOUS ASYMMETRIC SIGNAL TARGETING ALTERNATING RADIO FREQUENCY (PASTAR) FOR MAGNETIC RESONANCE ANGIOGRAPHY

(71) Applicant: TOSHIBA MEDICAL SYSTEMS CORPORATION, Tochigi (JP)

(72) Inventors: Cheng Ouyang, Buffalo Grove, IL (US); Aiming Lu, Chicago, IL (US); Mitsue Miyazaki, Des Plaines, IL (US)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 610 days.

(21) Appl. No.: 14/230,384

(22) Filed: Mar. 31, 2014

(65) Prior Publication Data
US 2015/0276907 A1 Oct. 1, 2015

(51) Int. Cl.
| | |
|---|---|
| G01R 33/48 | (2006.01) |
| G01R 33/563 | (2006.01) |
| A61B 5/055 | (2006.01) |
| G01R 33/483 | (2006.01) |
| G01R 33/561 | (2006.01) |

(52) U.S. Cl.
CPC ........ G01R 33/56366 (2013.01); *A61B 5/055* (2013.01); *G01R 33/4835* (2013.01); *G01R 33/5611* (2013.01); *G01R 33/5616* (2013.01); *G01R 33/5635* (2013.01)

(58) Field of Classification Search
CPC ............ G01R 33/4835; G01R 33/5616; G01R 33/5635; G01R 33/56333; A61B 5/055
See application file for complete search history.

(56) References Cited

U.S. PATENT DOCUMENTS

| | | | | |
|---|---|---|---|---|
| 6,306,091 B1* | 10/2001 | Sumanaweera | ..... | G01S 7/52034 128/916 |
| 6,310,479 B1* | 10/2001 | Zhu | ........................ | A61B 5/055 324/312 |
| 6,564,080 B1 | 5/2003 | Kimura | | |
| 7,627,360 B2 | 12/2009 | Kimura | | |
| 2008/0061780 A1* | 3/2008 | Yamada | ............... | A61B 5/0263 324/309 |
| 2008/0064951 A1* | 3/2008 | Kitane | ................... | A61B 5/055 600/413 |

(Continued)

OTHER PUBLICATIONS

Kimura et al., "Practical Method of Quantifying Cerebral Blood Flow Using Pulsed Arterial Spin Labeling Correlation with Cold Xenon-CT Measurements", Proc. Intl. Soc. Magnetic Resonance in Medicine 9 (2001), p. 1570.

(Continued)

*Primary Examiner* — Clayton E Laballe
*Assistant Examiner* — Ruifeng Pu
(74) *Attorney, Agent, or Firm* — Nixon & Vanderhye P.C.

(57) ABSTRACT

A magnetic resonance imaging (MRI) system, method and/or computer readable medium is configured to effect MR imaging based upon arterial spin labeling (ASL) using a tagging image and a control image. The tagging image is based upon applying a tagging pulse train including a plurality of saturation pulses to a tagging area followed by applying a first imaging pulse train to an imaging area; and the control image is based upon applying a control pulse train to a control area followed by applying a second imaging pulse train to the imaging area. The tagging area, the control area, and the imaging area are located at respectively different positions in relation to the object being imaged.

16 Claims, 7 Drawing Sheets

(56) References Cited

U.S. PATENT DOCUMENTS

| | | | | |
|---|---|---|---|---|
| 2012/0271147 A1* | 10/2012 | Kim | ............... | A61B 5/055 600/410 |
| 2013/0336565 A1* | 12/2013 | Bakker | ............... | G06T 7/0024 382/131 |
| 2015/0092917 A1* | 4/2015 | Roessl | ............... | A61B 6/032 378/62 |
| 2015/0338489 A1* | 11/2015 | Nitta | ............... | A61B 5/14507 324/309 |
| 2016/0033593 A1* | 2/2016 | Isoda | ............... | A61B 5/055 324/318 |

OTHER PUBLICATIONS

Kimura, Tokunori. "Non-Invasive Perfusion Imaging by Modified STAR Using Asymmetric Inversion Slabs (ASTAR)," 2000, Japanese Journal of Magnetic Resonance in Medicine. vol. 20, No. 8.pp. 374-385, (with English Abstract).

Wu et al., "Noncontrast-Enhanced Three-Dimensional (3D) Intracranial MR Angiography Using Pseudocontinuous Arterial Spin Labeling and Accelerated 3D Radial Acquisition", Magnetic Resonance in Medicine 69:708-715 (2013).

Tan et al., "Fast Inversion Recovery Magnetic Resonance Angiography of the Intracranial Arteries", Magnetic Resonance in Medicine 63:1648-1658 (2010).

Kimura et al., "Practical Method of Quantifying Cerebral Blood Flow Using Arterial Spin Labeling : Numerical Simulation and Correlation of Pulsed ASL and Cold Xenon-CT CBF", 2002, Japanese Journal of Magnetic Resonance in Medicine. vol. 22, No. 3, pp. 111-125 (with English Abstract).

Dai et al., "Continuous Flow-Driven Inversion for Arterial Spin Labeling Using Pulsed Radio Frequency and Gradient Fields", Magnetic Resonance in Medicine 60:1488-1497 (2008).

Ouyang et al., "Pseudo-Continuous Transfer Insensitive Labeling Technique", Magnetic Resonance in Medicine 66:768-776 (2011).

* cited by examiner

PSEUDO-CONTINUOUS ASYMMETRIC SIGNAL TARGETING ALTERNATING RADIO FREQUENCY (PASTAR) FOR MAGNETIC RESONANCE ANGIOGRAPHY

FIELD

The subject matter below relates generally to magnetic resonance imaging (MRI). In particular, the subject matter relates to magnetic resonance angiography (MRA) based upon arterial spin labeling (ASL).

DETAILED DESCRIPTION

Figure 1:
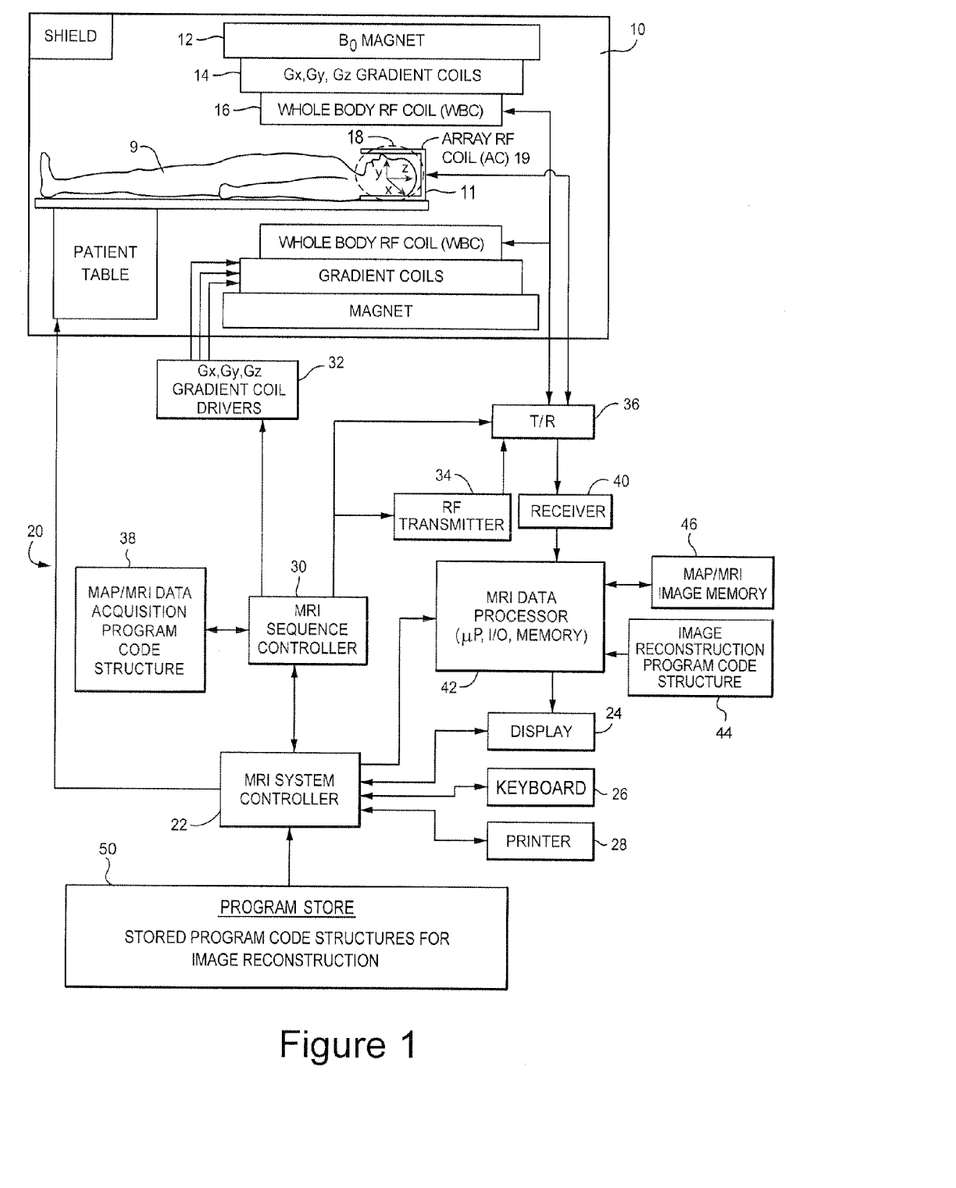
FIG. 1 is a high-level schematic block diagram of an MRI system adapted for improved ASL imaging, in accordance with one or more embodiments.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field $B_0$ magnet 12, a Gx, Gy and Gz gradient coil set 14 and a large whole body RF coil (WBC) assembly 16. Along the horizontal axis of this cylindrical array of elements is an imaging volume 18 shown as substantially encompassing the head of a patient 9 supported by a patient table 11. One or more smaller array RF coils 19 might be more closely coupled to the patient head in imaging volume 18. As those in the art will appreciate, compared to the WBC (whole body coil), relatively small coils and/or arrays such as surface coils or the like are often customized for particular body parts (e.g., arms, shoulders, elbows, wrists, knees, legs, chest, spine, etc.). Such smaller RF coils are herein referred to as array coils (AC) or phased array coils (PAC). These may include at least one coil configured to transmit RF signals into the imaging volume and a plurality of receiver coils configured to receive RF signals from an object, such as the patient head in the example above, in the imaging volume.

An MRI system controller 22 has input/output ports connected to a display 24, keyboard 26 and printer 28. As will be appreciated, the display 24 may be of the touchscreen variety so that it provides control inputs as well and a mouse or other I/O device(s) may be provided.

The MRI system controller 22 interfaces with MRI sequence controller 30 which, in turn, controls the Gx, Gy and Gz gradient coil drivers 32, as well as the RF transmitter 34 and the transmit/receive switch 36 (if the same RF coil is used for both transmission and reception). The MRI sequence controller 30 includes suitable program code structure 38 for implementing MRI imaging (also known as nuclear magnetic resonance, or NMR, imaging) techniques including parallel imaging. As described below, sequence controller 30 may be configured to apply a predetermined tagging pulse sequence and a predetermined control pulse sequence, in order to obtain corresponding tagging and control images from which a diagnostic MRI image is obtained. MRI sequence controller 30 may also be configured for EPI imaging and/or parallel imaging. Moreover, MRI sequence controller 30 may facilitate one or more preparation scan (prescan) sequences, and a scan sequence to obtain a main scan MR image (sometimes referred to as a diagnostic image).

The MRI system 20 includes an RF receiver 40 providing input to data processor 42 so as to create processed image data, which is sent to display 24. The MRI data processor 42 is also configured for access to previously generated MR data, images, and/or maps, and/or system configuration parameters 46 and MRI image reconstruction program code structures 44 and 50.

Also illustrated in FIG. 1 is a generalized depiction of an MRI system program store 50 where stored program code structures (e.g., for image reconstruction of control and tagging images, generation of subtracted image, etc. as described below) are stored in non-transitory computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments described hereinbelow. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an image reconstruction process and/or sometimes the generation of a subtracted image from control and tagging images, as described below, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the internal physical structures of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, causes a particular sequence of operational states to occur and be transitioned through within the MRI system.

Magnetic resonance angiography (MRA) is a MRI technique used to obtain images of blood vessels. MRA is often used to generate images of arteries (and sometimes, veins) in order to detect stenosis (abnormal narrowing) or other abnormalities. A variety of techniques are used to generate the images based on blood flow effects or on contrast. Contrast enhanced techniques require that a contrast agent is introduced into the object being imaged. Non-contrast enhanced MRA techniques do not require a contrast agent.

One type of non-contrast enhanced MRA utilizes flow-related enhancement of blood into a region previously saturated by selective excitation. This class includes so called time-of-flight (TOF) techniques and spin-labeling or tagging techniques. TOF is a non-contrast enhanced MRA technique that uses a short echo time and flow compensation to make flowing blood much brighter than stationary tissue.

Arterial spin labeling (ASL) is of particular interest for non-contrast enhanced MRA applications. Similar to TOF, ASL relies upon the inflow of blood into the volume being imaged; however, ASL uses separate control and tag pulse sequences to label (i.e., tag) spins of inflowing blood differently. Separate images are generated based upon the control pulse sequence and the tag pulse sequence. An image generated based upon a control pulse sequence is referred to as a "control image," and an image generated based upon a tag pulse sequence is referred to as a "tag image." By subtracting the tagging image from the control image, or vice versa, an MRA image can be obtained with near zero background.

Pulsed ASL (PASL) MRA and pseudo-continuous ASL (pCASL) are two distinct types of ASL-based MRA that have been proposed in the literature.

Tan et al., "Fast Inversion Recovery Magnetic Resonance Angiography of the Intracranial Arteries," Magnetic Resonance in Medicine 63:1648-1658 (2010), provides a description of a PASL technique. In PASL, a single inversion pulse is used for labeling. Specifically, in the technique described in Tan et al., during a first inversion cycle a nonselective inversion pulse is applied, whereby the inversion time (TI) is chosen to null the signal of the inverted blood, and in a second inversion cycle, a selective inversion is applied to the targeted axial imaging slab. Blood proximal to the inversion slab remains fully or highly magnetized and flows into the imaging slab during a prescribed in-flow interval, set to equal TI of the first cycle. A complex difference between signals acquired from the two inversion cycles eliminates static tissue in the imaging slab and generates an angiogram due to the inflowing, magnetized blood.

However, PASL MRA is highly sensitive to the selection of TI. The limitation of applying PASL techniques for MRA is mainly due to long and varied arterial transit time (ATT) for the labeled (i.e., tagged) spins to flow from the tagging slab to the imaging slab.

Figure 2:
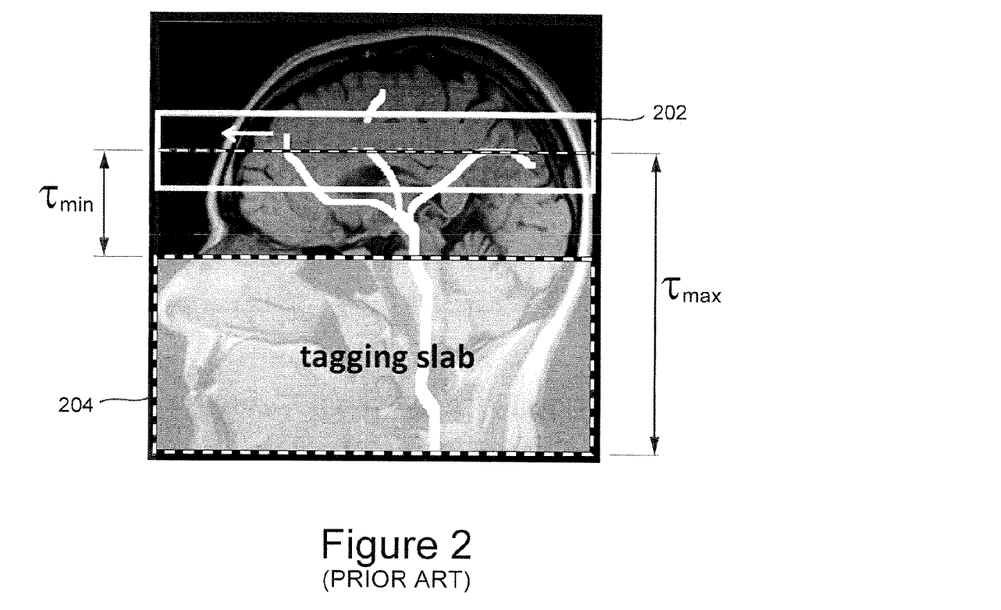
FIG. 2 illustrates a sketch showing the location of imaging and tagging areas according to a first conventional ASL imaging technique.

For example, as shown in FIG. 2, in healthy human brain, the tagging slab 204 of PASL MRA is usually wide, more than 10 cm, covering the whole internal carotid arteries (ICAs) in FOV and part of Circle of Willis (COW). Thus, the ATT from the upper edge (i.e., the edge closer to the imaging slab 202) of the tagging slab 204 to the imaging brain parenchyma ($\tau_{min}$) can be from 65 ms to 800 ms depending on the imaging slice 202 position, while the ATT from the bottom edge (i.e., the edge farther from the imaging slab 202) to the upper edge of the tagging slab 204 is at the scale of 400-800 ms ($\tau_{max}$-$\tau_{min}$). $\tau$ may be determined as the time for labeled blood to reach the mid point of the imaging slab 202. In PASL the tagging slab is set to a substantial width so that a sufficiently large amount of blood will be tagged in order to generate an adequately strong ASL signal in the imaging area.

Therefore, due to the prolonged and varied ATT in imaging tissue, PASL MRA applications usually face the challenge of reduced blood signal and image blurring by tag decay due to $T_1$ recovery.

In pCASL, a series of discrete pulses with small flip angles is used for continuous tagging. Dai et al., "Continuous Flow-Driven Inversion for Arterial Spin Labeling Using Pulsed Radio Frequency and Gradient Fields," Magnetic Resonance in Medicine 60:1488-1497 (2008), and Wu et al., "Noncontrast-Enhanced Three-Dimensional (3D) Intracranial MR Angiography Using Pseudocontinuous Arterial Spin Labeling and Accelerated 3D Radial Acquisition," Magnetic Resonance in Medicine 69:708-715 (2013), provide descriptions of a MRA techniques using pCASL. PCASL is sometimes also referred to as pulsed CASL.

Figure 3A:
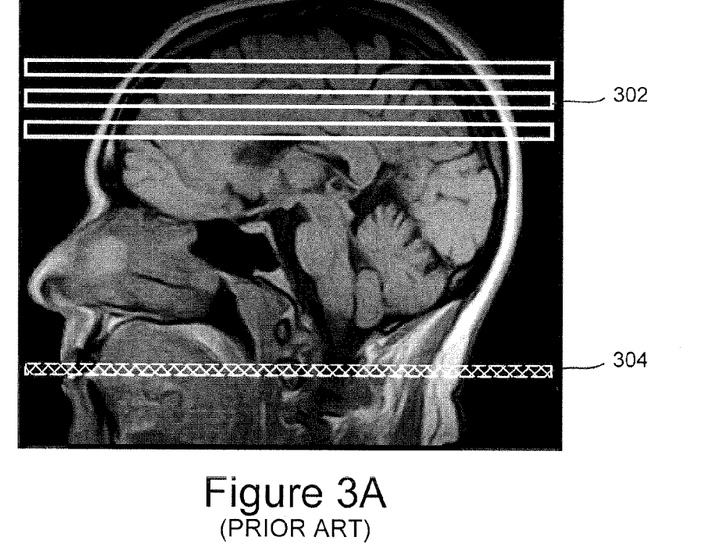
FIG. 3A illustrates a sketch showing the location of imaging, tagging, and control areas according to a second conventional ASL imaging technique.
Figure 3B:
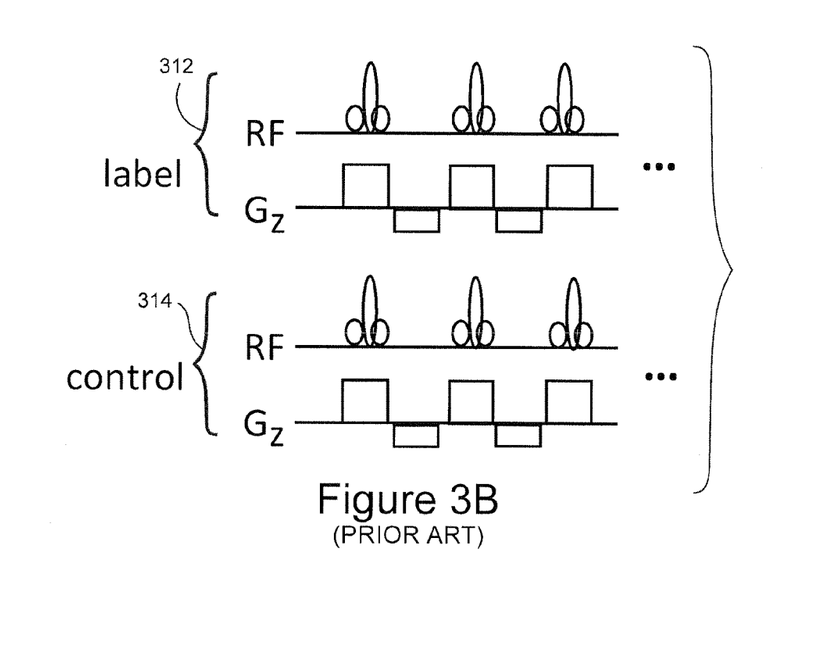
FIG. 3B illustrates a sketch showing pulse sequences for labeling and control according to the second conventional ASL imaging technique.

FIG. 3A illustrates the geometry of pCASL which positions a tagging plane 304 below the imaging area 302, around the ICA level.

pCASL MRA uses continuous tagging in a thin tagging plane, and is thus immune to ATT effects. Dai el al. introduced a technique for continuous tagging without requiring specialized hardware. The tagging duration of pCASL MRA is configured between 1-5 seconds, therefore, at the time of imaging, the tagged blood signal has reached steady state in the imaging slab. In the technique described by Wu et al., the RF phase cycling in the tagging stage is set such that spins at the labeling plane see RF pulses with the same phase. In this condition, the spins passing through this labeling plane undergo adiabatic inversion. In the control state, the RF pulse train and the gradients are the same as in the label state, while the RF phase is cycled such that spins at the labeling plane see RF pulses having a phase of n relative to the previous pulse, leading to limited effect on the passing spins. In the implementation of Wu et al., a Hanning window-shaped RF pulse of 500 ms duration was performed periodically with a 1200 ms spacing between RF pulses. Dai et al., describes a pCASL technique using a Hanning window-shaped pulse of 500 microseconds duration, a spacing between two Hanning pulses of 1500 microseconds, and a labeling duration of 1.5 seconds. However, one of the major challenges of pCASL MRA is that it is highly sensitive to off-resonance artifact. Off-resonance artifact in pCASL is particularly substantial in intracranial applications where the tagging locates around the neck area. FIG. 3B illustrates an example pCASL pulse sequence comprising a labeling sequence 312 and a control sequence 314. As illustrated, sequences of 0-degree-phase pulses (with a flip angle, for example, of about 20°) and a sequence of 180-degree-phase pulses are applied, respectively, as a labeling sequence and a control sequence, with the same or similar gradients $G_2$. However, pCASL is sensitive to numerous parameters.

ASTAR (Asymmetric Signal Targeting Alternating Radiofrequency), which is a modified version of the PASL technique of STAR (Signal Targeting Alternating Radiofrequency), is used to measure perfusion (i.e. flow of blood) by using asymmetric inversion slabs between control and tag acquisitions. See Kimura, Tokunori, "Non-Invasive Perfusion Imaging by Modified STAR Using Asymmetric Inversion Slabs (ASTAR)," Japanese Journal of Magnetic Resonance in Medicine, vol. 20, No. 8. pp. 374-385 (2000); see also U.S. Pat. No. 6,564,080, which is hereby incorporated by reference in its entirety. Whereas STAR suffered from issues related to suppression of venous inflow and balancing the stationary tissue signals induced by inconsistent magnetization transfer effect between tag and control, ASTAR successfully overcame these issues.

Figure 4A:
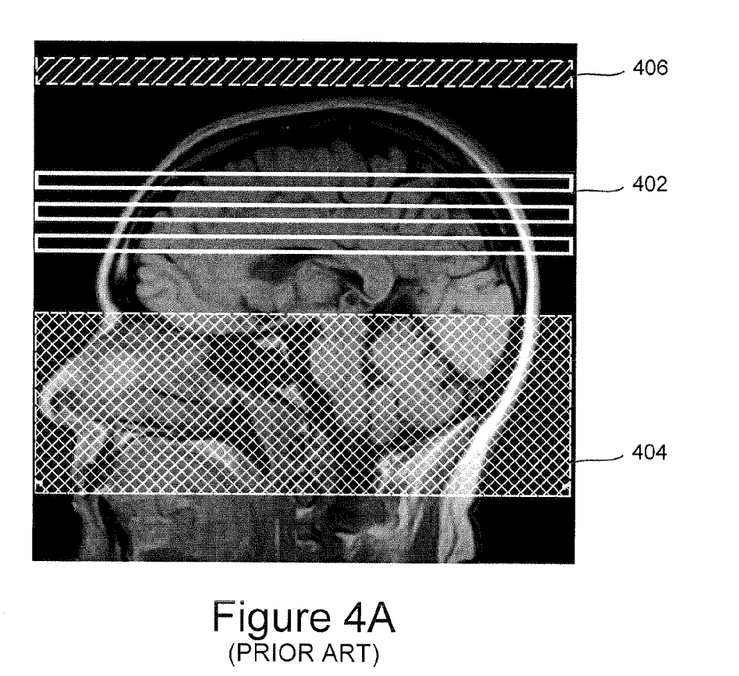
FIG. 4A illustrates a sketch showing the location of imaging, tagging, and control areas according to a third conventional ASL imaging technique.

The geometry of ASTAR, e.g., the positioning of the respective tagging, control, and imaging areas, is shown in FIG. 4A. In order not to overlap the control slab 406 to the tissue including vein, the control and tag slabs (406 and 404, respectively) may be arranged spatially asymmetrically with respect to the imaging area 402 in a manner that preserves the same offset and modulation frequency.

Figure 4B:
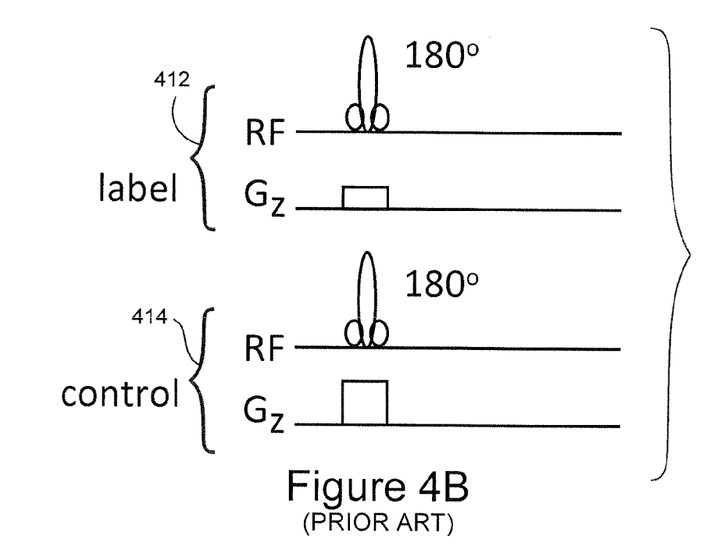
FIG. 4B illustrates a sketch showing pulse sequences for labeling and control according to the third conventional ASL imaging technique.

A pulse sequence for ASTAR is illustrated in FIG. 4B. As shown, a labeling sequence 412 and a control sequence 414 are employed, and applied respectively in the tag slab 404 and control slab 406. The label sequence 412 comprises one selective inversion pulse (e.g. 180-degree pulse), and the control sequence 414 comprises a single pulse the same as the label pulse but applied with a gradient of higher amplitude.

Embodiments disclosed herein include a novel pseudo-continuous ASL method for MRA applications referred to as pseudo-continuous ASTAR (pASTAR). pASTAR modifies the conventional ASTAR technique such that, among other advantages, the issue of sensitivity to ATT in PASL MRA is reduced, and off-resonance artifact in pCASL MRA is reduced.

Figure 5:
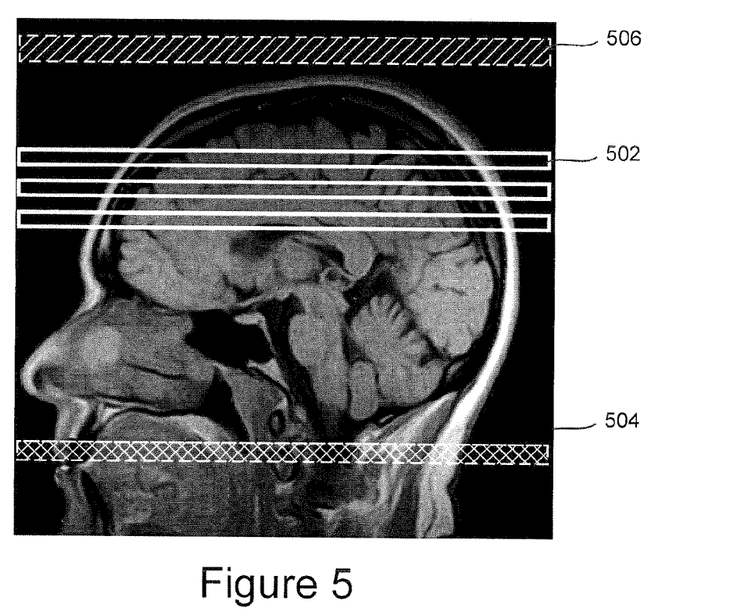
FIG. 5 illustrates a sketch showing the location of imaging, tagging, and control areas, in accordance with one or more embodiments.

The geometry of pASTAR, in an intracranial MRA application, for example, is shown in FIG. 5. The tagging slab 504 of pASTAR is reduced to a very thin slice (around 1-5 cm), and the tagging location is placed close to COW. Under these geometrical conditions, the ATT from the tagging slice 504 to the imaging slice 502 is almost uniform and it avoids the extra ATT from ICAs to COW, therefore, it reduces signal loss due to T1 recovery. The control slab 506 is located, for example, outside the area in which blood marked by the control area would enter the imaging area through, for example, veins.

Figure 6:
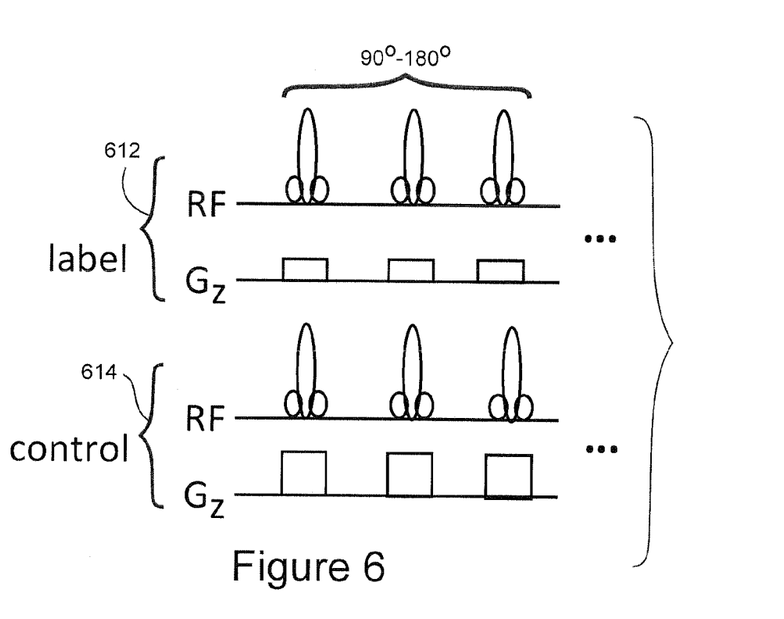
FIG. 6 illustrates a sketch showing pulse sequences for labeling and control, in accordance with one or more embodiments.

An example pulse sequence for pASTAR is shown in FIG. 6. The pASTAR pulse sequence includes a labeling pulse sequence 612 and a control pulse sequence 614. Compared to the ASTAR sequence (e.g., shown in FIG. 4B), there are at least three modifications in the pASTAR sequence: (a) whereas ASTAR used an inversion pulse for labeling, pASTAR uses a saturation pulse between 90 to 180 degrees for labeling; (b) whereas ASTAR used a single labeling pulse, pASTAR uses a repetition of tagging pulses, amplitude-changing gradient spoilers and delays are implemented, with the tagging duration being in the range of 1-3 seconds; and (c) whereas ASTAR used a single control pulse, in pASTAR the control sequence includes the same number of saturation pulses as the labeling sequence.

pASTAR and its applications have multiple advantages compared to conventional ASL MRA techniques. When compared to PASL MRA, pASTAR MRA is substantially immune to ATTs due to continuous tagging. pASTAR may also have reduced ATT from tagging slab to imaging slices by having the tagging slice placed closer to the imaging slab. Also, in pASTAR, by placing the tagging area close to the imaging area, the signal loss of the labeled blood due to T1 recovery is reduced.

Compared to pCASL and pTILT (Ouyang et al., "Pseudo-Continuous Transfer Insensitive Labeling Technique," Magnetic Resonance in Medicine 66:768-776 (2011)), which are highly vulnerable to off-resonance effects, pASTAR is relatively insensitive to magnetic field inhomogeneity artifacts and thus the labeling efficiency is substantially independent of $B_0$ inhomogeneities. For example, the specific RF pulses used in pCASL is highly sensitive to $B_0$, whereas the RF pulses used in pASTAR are relatively insensitive to $B_0$ inhomogeneity. This is particularly advantageous for intracranial MRA imaging, since the tagging location for ASL MRA is usually around the neck which has an inhomogeneous field map.

Additionally, when compared to pCASL in which the tagging efficiency in the function of spin velocity is not uniform (e.g., high efficiency for fast flow and low efficiency for slow flow), pASTAR has a more uniform velocity profile with substantially equal tagging efficiency for both fast and slow flows. Therefore, pASTAR allows for ECG-gating free applications.

Still further, compared to pCASL which due to the nature of its tagging pulses has an RF duty cycle greater than 50%, pASTAR generates low RF power due to its small RF duty cycle (e.g., around 20%) and thus yields more preferable specific absorption rates (SAR) with respect to the RF power absorbed by the imaged subject.

Figure 7:
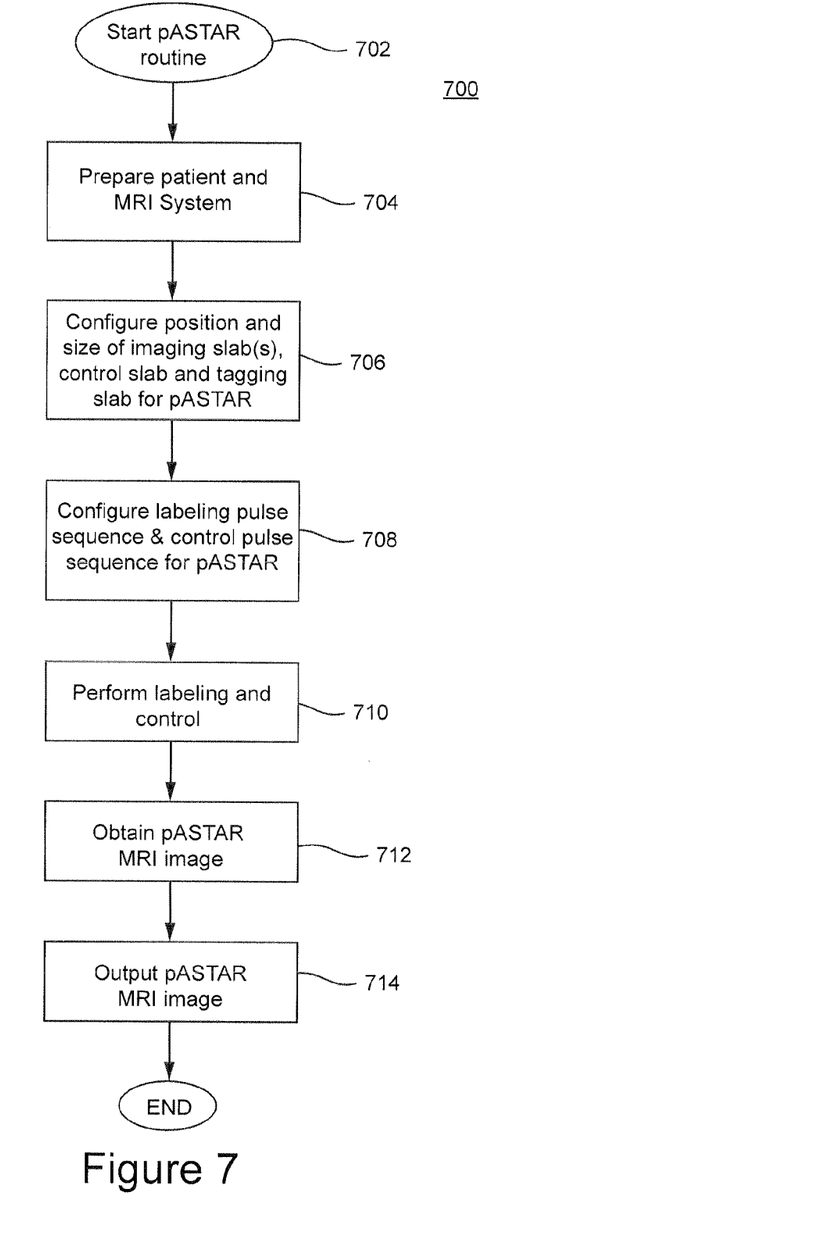
FIG. 7 illustrates a flowchart of a technique for improved ASL imaging, in accordance with one or more embodiments.

FIG. 7 illustrates a routine 700 for obtaining improved ASL images, in accordance with one or more embodiments. Routine 700 may be performed on a system such as that shown in FIG. 1. It will be understood that one or more of the operations 702-714 of routine 700 may be performed in an order other than that shown in FIG. 7, may not be performed, or may be combined with one or more other operations.

After entering the routine at 702, at operation 704, the patient and the MRI system are prepared for imaging using the pASTAR technique. Operation 704 may include positioning the patient and/or the part of the patient to be imaged in relation to transmit and/or receive coils of the MRI system, and setting of general parameters and/or configuration options for performing imaging.

Examples described above in relation to FIG. 5 illustrate the application of pASTAR to image an intracranial area of a patient. However, pASTAR can be applied to image other parts, such as, but not limited to, kidneys, feet, and specific muscles of the patient, with appropriate configurations of the system and positioning of the patient. As described below, certain configurations, such as, for example, tagging slice thickness, the number of tagging pulses, a total duration of tagging, and time delay between tagging pulses can be adjusted in a respective manner based upon selected characteristics of the object image. For example, configurations may be set and/or adjusted in accordance with the flow speed of the specific part of the body or organ being imaged.

In some 3D imaging embodiments, 2D sequences of the corresponding 3D sequences are used as independent preparation scans while varying the tagging pulse delays between, in order to determine an interval between pulses that would improve efficiency. Alternatively, in some embodiments, the 2D sequences of the corresponding 3D sequences can be used as independent preparation scans with varying tagging slice thickness.

At operation 706, a tagging area, a control area, and an imaging area in accordance with the pASTAR technique are configured. According to an embodiment, the tagging area is a thin slice configured to have a thickness of 1-5 centimeters. Other parameters that are configured for the tagging area may include its location relative to the object, and the angle (e.g. the tilt relative to the z-axis) of the slice. For example, the location of the tagging area may be specified by identifying the center of the tagging slice. The angle of the slice may, for example, be specified in degrees relative to the z-axis, where the z-axis is deemed to correspond to the body axis of the patient. By default each of the slices (i.e. tagging, imaging, control areas) are configured to be transverse (i.e. at a right angle) to the z-axis. For some imaging applications, it may be desired that the imaging area is at an angle other than a right angle to the z-axis. For example, tagging area orientation (see e.g., tagging slab 504' and control slab 506' shown in FIG. 8) can be tilted or oblique in order to observe target object, such as cerebrospinal fluid (CSF) movement in intracranial and intraspinal region.

Figure 8:
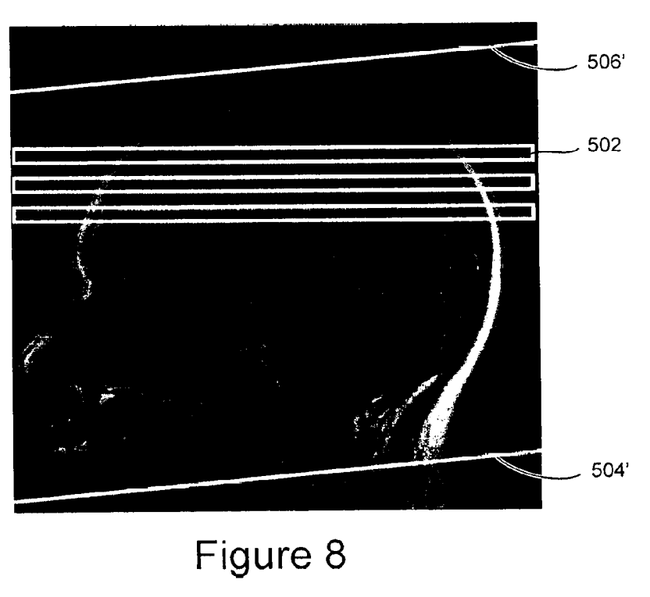
FIG. 8 illustrates a sketch showing example tilted or oblique orientation tagging and control areas in accordance with one or more embodiments.

For the control area and the imaging area too, their respective thicknesses, locations and/or angles may be configured. Additionally, in some embodiments, a number of slices may be configured for the imaging area. If the imaging area is configured to have more than one slice, each slice may yield a separate MRI image. Example positioning, for an intracranial application, of the tagging 504, imaging 502 and control 506 areas according to pASTAR are illustrated in FIG. 5. The configuration of the slice/slab thickness, angle, location etc., may be set differently in accordance with the specific object being imaged. For example, the configuration of the tagging slice thickness may differ in accordance with the blood flow speed associated with the object being imaged. 504' and 506' shown in FIG. 8 illustrate example tilted or oblique orientation of the tagging slab and control slab, respectively, for some intracranial applications.

The tagging area is not required to be at any particular distance from the imaging area, and the distance (e.g. distance from the z-axis center of the tagging area to the center of the z-axis center of the imaging area) may be set in accordance with the patient's body area to be imaged. A thin tagging area is provided so that only minimal tagging slice profile error is included, if any, in the final image. According to an embodiment, the control area is located completely outside of the area which contains veins that extend into the imaging area. For example, in the example intracranial application shown in FIG. 5, the control slab 506 is located entirely outside the area of the brain that contains veins.

At operation 708, at least one pulse sequence in accordance with the pASTAR technique is configured. According to an embodiment, a configured pASTAR pulse sequence includes a tagging pulse sequence and a control pulse sequence. Example tagging 612 and control 614 pulse sequences are illustrated in FIG. 6.

In some embodiments, the tagging pulse sequence and the control pulse sequence are each configured with an imaging pulse train. Thus, in some embodiments, the tagging pulse sequence includes a train of tagging pulses and a train of imaging pulses; and the control pulse sequence includes a train of control pulses and a train of imaging pulses.

With respect to the train of tagging pulses, the number of pulses, the total duration of the train of tagging pulses, and time delay between the tagging pulses can be adjusted in accordance with the flow speed of the object to be imaged. In some embodiments, the flip angle and/or the pulse width of the tagging pulses can be configured.

According to an embodiment, tagging pulse sequence 612 may include pseudo-continuous tagging over a time interval of 1 to 3 seconds with multiple short pulses being applied. The relatively long duration of between 1 to 3 seconds of the tagging time interval, enables the tagging to cover a complete cardiac cycle. The intervals between the tagging pulses may be configured for durations between 20-40 milliseconds in a manner dependent of the flow speed of the target object or organ. The intervals between the tagging pulses, and/or the sum of the width of a tagging pulse and the interval between two pulses, may be configured so that it is inversely proportional to the flow speed of the organ or object targeted for imaging. The multiple short pulses use a saturation pulse with flip angle of more than 90 and less than 180 degrees.

In an example MRA application for imaging intracranial blood flow, the tagging slice thickness and the time interval between two consecutive tagging pulses are adjusted specifically to match the intracranial blood flow. According to an example embodiment, one tagging segment includes the tagging pulse (6 milliseconds), an amplitude-changing gradient spoiler (4 milliseconds) and a time delay (20 milliseconds) between consecutive pulses, therefore, one repetition of tagging is, in this example, 30 milliseconds in duration. To achieve 3 seconds tagging in total, a 100 repetitions of the tagging is included in the tagging pulse train. If the tagging area thickness is configured to be 1 cm, then the tagging will be sensitive to velocities from 0 to 33.3 cm/s, which is the normal range of intracranial blood flow.

At operation 710, the configured tagging pulse sequence and control pulse sequence are applied. The train of tagging pulses of the tagging pulse sequence is applied to the tagging area, and the train of control pulses of the control pulse sequence is applied to the control area respectively. The control pulse works as a pair with the tagging pulse, and is applied in order to cancel the magnetization transfer effect within the imaging slab. According to an embodiment, following the application of a tagging pulse train or a control pulse train, an imaging pulse train is applied to obtain the respective tag images and control images. Any imaging pulse sequences can be thereafter used with pASTAR, such as, but not limited to, 2D/3D Field Echo (FE), Fast Field Echo (FFE), Fast Spin Echo (FSE), Steady State FSE (SSFSE), Balanced Steady State Free Precision (bSSFP), Ultrashort Echo Time (UTE), etc, imaging pulse sequences. In a particular embodiment, the imaging pulse trains in the tagging pulse sequence and the control pulse sequence are identical.

At operation 712, MRA images are obtained by subtracting tag images from the corresponding control images. In some embodiments, in order to minimize the appearance of magnetization transfer effects in the final images, operations 710 and 712 are performed so that echo data for control images and tag images are acquired sequentially in time. However, other orders of acquisition for control images and tagging images are possible, and are contemplated as embodiments. Kimura et al, incorporated above, describes one or more techniques which may be used in embodiments to determine the subtracted image from the control and tag images.

At operation 714, the obtained MRA images are output to a display, to storage, directed to a printer, or communicated to another device for further processing.

Because the new pASTAR sequences use relatively simple, e.g. "normal", saturation pulses, it is not so sensitive to blood velocity vis-à-vis tagging efficiency and it is otherwise easier to implement and/or provides improved results.

While certain embodiments have been described, these embodiments have been presented by way of example only and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) system for effecting MR imaging based upon arterial spin labeling (ASL), said MRI system comprising:
   an MRI gantry including a static magnetic field coil, gradient magnetic field coils, at least one radio frequency (RF) coil configured to couple with an object located in an imaging volume;
   an MRI sequence controller configured to perform an RF pulse sequence comprising (1) applying a tagging pulse train including a plurality of saturation pulses to a tagging area followed by applying a first imaging pulse train to an imaging area, and (2) applying a control pulse train to a control area followed by applying a second imaging pulse train to the imaging area, wherein the tagging area, the control area, and the imaging area are located at respectively different positions in relation to the object;
   and
   at least one digital data processor configured to:
   receive first digital data and second digital data corresponding respectively to NMR signals responsive to the first imaging pulse train and to NMR signals responsive to the second imaging pulse train;
   generate at least one tag image from the received first digital data and at least one control image from the received second digital data;
   form a diagnostic MR image of the object based upon the at least one tag image and the at least one control image; and
   output the diagnostic MR image to a display, or data storage in a non-transient digital data storage medium, or an outbound data transmission port.

2. The MRI system of claim 1, wherein the MRI sequence controller is further configured to include the same number of saturation pulses in the tagging pulse train and the control pulse train.

3. The MRI system of claim 1, wherein the MRI sequence controller is further configured to set a flip angle between 90 to 180 degrees for the saturation pulses.

4. The MRI system of claim 3, wherein the flip angle of saturation pulses of the tagging pulse train and the flip angle of saturation pulses of the control pulse train are identical.

5. The MRI system of claim 1, wherein the MRI sequence controller is further configured to set respective tagging pulses of the tagging pulse train to include one or more amplitude-changing gradient spoiler pulses.

6. The MRI system of claim 1, wherein a width of the tagging area is set so that the arterial transit time (ATT) from the tagging area to the imaging area is substantially uniform.

7. The MRI system of claim 6, wherein the tagging area is a thin slice configured to be between 1-5 centimeters in thickness.

8. The MRI system of claim 1, wherein the MRI sequence controller is further configured to apply the tagging pulse train over a duration of 1 to 3 seconds.

9. The MRI system of claim 8, wherein the MRI sequence controller is further configured to set intervals between consecutive tagging pulses based upon blood flow speed to be imaged in a specific part of the object being imaged.

10. The MRI system of claim 1, wherein the MRI sequence controller is further configured to apply the tagging pulse train over a length of time exceeding a cardiac cycle.

11. The MRI system of claim 1, wherein the MRI sequence controller is further configured to set the tagging and control areas at an oblique angle in relation to the object.

12. The MRI system of claim 1, wherein said applying the tagging pulse train followed by the first imaging pulse train, and said applying the control pulse train followed by the second imaging pulse train is performed alternately.

13. The MRI system of claim 1, wherein the MRI sequence controller is further configured to apply two-dimensional (20) sequences corresponding to three-dimensional (30) sequences as independent preparation scans with varying tagging pulse delays to determine a desired tagging pulse delay, and to set an interval between consecutive tagging pulses in the tagging pulse train in accordance with the determined desired pulse delay.

14. The MRI system of claim 1, wherein the MRI sequence controller is further configured to apply 20 sequences corresponding to 30 sequences as independent preparation scans with varying tagging slice thicknesses to determine a desired tagging slice thickness, and to set the tagging area to have a width corresponding to the determined desired tagging slice thickness.

15. A magnetic resonance imaging (MRI) method for effecting MR imaging based upon arterial spin labeling (ASL), said MRI method comprising:
   placing an object into an MRI gantry including a static magnetic field coil, gradient magnetic field coils, at least one radio frequency (RF) coil configured to couple with an imaging volume;
   using an MRI sequence controller to perform an RF pulse sequence comprising (1) applying a tagging pulse train including a plurality of saturation pulses to a tagging area followed by applying a first imaging pulse train to an imaging area, and (2) applying a control pulse train to a control area followed by applying a second imaging pulse train to the imaging area,
   wherein the tagging area, the control area, and the imaging area are located at respectively different positions in relation to the object;
   receiving first digital data and second digital data corresponding respectively to echo data responsive to the first imaging pulse train and to echo data responsive to the second imaging pulse train;
   generating at least one tag image from the received first digital data and at least one control image from the received second digital data;
   forming a diagnostic MR image of the object based upon the at least one tag image and the at least one control image; and
   outputting the diagnostic MR image to a display, or data storage in a non-transient digital data storage medium, or an outbound data transmission port.

16. A non-transitory computer readable storage medium, having executable computer program instructions recorded thereon, which when executed by at least one processor of a magnetic resonance imaging (MRI) system having an MRI gantry including a static magnetic field coil, gradient magnetic field coils, at least one radio frequency (RF) coil, causes the at least one processor to generate a final MRI image an object, by performing operations comprising:

configuring a sequence controller to perform an RF pulse sequence comprising (1) applying a tagging pulse train including a plurality of saturation pulses to a tagging area followed by applying a first imaging pulse train to an imaging area, and (2) applying a control pulse train to a control area followed by applying a second imaging pulse train to the imaging area, wherein the tagging area, the control area, and the imaging area are located at respectively different positions in relation to the object;

receiving first digital data and second digital data corresponding respectively to echo data responsive to the first imaging pulse train and to echo data responsive to the second imaging pulse train;

generating at least one tag image from the received first digital data and at least one control image from the received second digital data;

forming a diagnostic MR image of the object based upon the at least one tag image and the at least one control image; and outputting the diagnostic MR image to a display, or data storage in a non-transient digital data storage medium, or an outbound data transmission port.

* * * * *